(12) United States Patent
Spilburg

(10) Patent No.: US 9,107,825 B2
(45) Date of Patent: Aug. 18, 2015

(54) METHODS AND FORMULATIONS FOR ENHANCING THE ABSORPTION AND GASTRO-INTESTINAL BIOAVAILABILITY OF HYDROPHOBIC DRUGS

(71) Applicant: Zomanex, LLC, Hendersonville, NC (US)

(72) Inventor: Curtis A. Spilburg, Hendersonville, NC (US)

(73) Assignee: ZOMANEX, LLC, Chesterfield, MO (US)

( * ) Notice: Subject to any disclaimer, the term of this patent is extended or adjusted under 35 U.S.C. 154(b) by 0 days.

(21) Appl. No.: 13/717,124

(22) Filed: Dec. 17, 2012

(65) Prior Publication Data

US 2013/0108689 A1    May 2, 2013

Related U.S. Application Data

(63) Continuation of application No. 11/291,126, filed on Nov. 30, 2005, now abandoned, which is a continuation-in-part of application No. 11/149,862, filed on Jun. 10, 2005, now abandoned, and a continuation-in-part of application No. 10/140,620, filed on May 7, 2002, now abandoned.

(51) Int. Cl.
*A61K 9/127* (2006.01)
*C12N 15/88* (2006.01)
*A61K 47/28* (2006.01)

(52) U.S. Cl.
CPC ............ *A61K 9/127* (2013.01); *A61K 9/1272* (2013.01); *C12N 15/88* (2013.01); *A61K 47/28* (2013.01)

(58) Field of Classification Search
CPC ........ A61K 47/24; A61K 9/17; A61K 9/2013
See application file for complete search history.

(56) References Cited

U.S. PATENT DOCUMENTS

| | | | |
|---|---|---|---|
| 4,229,360 A | 10/1980 | Schneider | |
| 4,247,411 A | 1/1981 | Vanlerberghe | |
| 4,311,712 A | 1/1982 | Evans | |
| 4,348,384 A | 9/1982 | Horikoshi et al. | |
| 4,508,703 A | 4/1985 | Redziniak et al. | |
| 4,621,023 A | 11/1986 | Redziniak | |
| 4,704,284 A * | 11/1987 | Beatty et al. | 424/469 |
| 4,744,989 A * | 5/1988 | Payne et al. | 424/490 |
| 4,830,858 A | 5/1989 | Payne | |
| 4,963,362 A | 10/1990 | Rahman | |
| 5,015,483 A | 5/1991 | Haynes | |
| 5,118,671 A | 6/1992 | Bombardelli et al. | |
| 5,139,803 A | 8/1992 | Haynes | |
| 5,169,636 A | 12/1992 | Nanba et al. | |
| 5,202,126 A | 4/1993 | Perrier et al. | |
| 5,244,887 A | 9/1993 | Straub | |
| 5,290,562 A | 3/1994 | Meybeck et al. | |
| 5,567,433 A | 10/1996 | Collins | |
| 5,716,928 A * | 2/1998 | Benet et al. | 514/20.5 |
| 5,932,562 A | 8/1999 | Ostlund, Jr. | |
| 5,989,583 A * | 11/1999 | Amselem | 424/439 |
| 6,054,144 A | 4/2000 | Burruano | |
| 6,063,776 A | 5/2000 | Ostlund | |
| 6,083,529 A | 7/2000 | Manzo | |
| 6,110,502 A | 8/2000 | Burruano | |
| 6,129,944 A | 10/2000 | Tiainen et al. | |
| 6,242,001 B1 | 6/2001 | Bruce | |
| 6,274,574 B1 * | 8/2001 | Akashe et al. | 514/182 |
| 6,312,703 B1 | 11/2001 | Orthoefer | |

FOREIGN PATENT DOCUMENTS

| | | |
|---|---|---|
| EP | 0736299 A1 | 10/1996 |
| EP | 0736299 B1 | 11/2001 |
| WO | WO 94/28876 | 12/1994 |
| WO | WO 00/45770 A2 | 8/2000 |
| WO | WO 0045770 A2 * | 8/2000 |

OTHER PUBLICATIONS

AH Lichtenstein, RH Deckelbaum. "Stanol/Sterol Ester—Containing Foods and Blood Cholesterol Levels." Circulation, vol. 103, 2001, pp. 1177-1179.*
CAS Registry Record for Fluvastatin (93957-54-1). Entered STN Dec. 30, 1984, 4 printed pages.*
J lsraelachvili, S Marcelja, RG Horn. "Physical Principles of Membrane Organization." Quarterly Reviews of Biophysics, vol. 13(2), 1980, pp. 121-200.*
ECA van Winden, W Zhang, DJA Crommelin. "Effect of Freezing Rate on the Stability of Liposomes During Freeze-Drying and Rehydration." Pharmaceutical Research, vol. 14, No. 9, 1997, pp. 1151-1160.
JN Israelachvili, S Marcelja, RG Horn. "Physical Principles of Membrane Organization." Quarterly Reviews of Biophysics, vol. 13 No. 2, 1980, pp. 121-164 are included.
Health Journal, "Pregnenolone", http://www.bodyandfitness.com/information/Womenhealth/Research/pregnenolone.htm, Mar. 8, 2001, (as of Internet Archive).
The Oxford English Dictionary 2nd Edition, Oxford University Press, 1989, Oxford English Dictionary Online: http://dictionary.oed.com/entrance.dtl.
Davis et al. "Transit of pharmaceutical dosage forms through small intestine", Gut 27:886-892, 1986.

* cited by examiner

*Primary Examiner* — Isaac Shomer
(74) *Attorney, Agent, or Firm* — Arnold & Porter LLP

(57) ABSTRACT

A hydrophobic drug delivery system that includes a plant derived sterol (stanol) or a sterol (stanol) derived ester, an emulsifier and an active, hydrophobic drug, all dissolved and then dried to form a liposome delivery system.

20 Claims, No Drawings

METHODS AND FORMULATIONS FOR ENHANCING THE ABSORPTION AND GASTRO-INTESTINAL BIOAVAILABILITY OF HYDROPHOBIC DRUGS

CROSS-REFERENCE TO RELATED APPLICATIONS

This application is a Continuation of U.S. Ser. No. 11/291,126 filed on Nov. 30, 2005 which is a Continuation-in-part of U.S. Ser. No. 11/149,862 filed Jun. 10, 2005 and U.S. Ser. No. 10/140,620 filed May 7, 2002, herein incorporated by reference in their entirety.

FIELD OF THE INVENTION

This invention relates to a general method for enhancing the bioavailability of hydrophobic drug active compounds, using naturally-occurring formulation ingredients that are present in the diet. Specifically, this invention is especially useful as a general formulation method for the delivery of drugs in dry form that heretofore have produced variable pharmacological responses, which are indicative of poor bioavailability.

BACKGROUND OF THE INVENTION

Many drugs are absorbed by passive diffusion through a hydrophobic cellular membrane, which does not participate in the absorption process. The amount of absorbed drug is controlled by two processes. First, a high concentration of the active substance at the membrane surface will enhance cellular absorption (Fick's Law). Since cells function in an aqueous environment, enhancing the water solubility of a drug increases its concentration at the locus of absorption. However, while greater water solubility may be expected to enhance the bioavailability of drugs, this is frequently not the case due to a second, competing process that affects the overall absorption process. The absorptive cell membrane is composed mainly of lipids that prevent the passage of hydrophilic compounds, but which are highly permeable to lipid soluble substances. Therefore, the design of bio-available drugs must balance two opposing forces. On the one hand, a drug that is very hydrophilic may have a high concentration at the cell surface but be impermeable to the lipid membrane. On the other hand, a hydrophobic drug that may easily "dissolve" in the membrane lipids may be virtually insoluble in water producing a very low concentration of the active substance at the cell surface.

To circumvent these problems, a number of strategies have been used to maintain the hydrophobicity of the drug and at the same time to provide a "packaging" matrix that increases its aqueous concentration. For example, emulsions can be prepared for the parenteral delivery of drugs dissolved in vegetable oil [Collins-Gold, L., Feichtinger, N. & Warnheim, T. (2000) "Are lipid emulsions the drug delivery solution?" Modern Drug Discovery, 3, 44-46.] Alternatively, artificial membranes of liposomes have been used to encapsulate a variety of drugs for different delivery routes, including oral, parenteral and transdermal [Cevc, G and Paltauf, F., eds., "Phospholipids: Characterization, Metabolism, and Novel Biological Applications", pp. 67-79, 126-133, AOCS Press, Champaign, Ill., 1995]. All these methods require amphiphiles, compounds that have a hydrophilic or polar end and a hydrophobic or nonpolar end, such as phospholipid, cholesterol or glycolipid or a number of food-grade emulsifiers or surfactants.

When amphiphiles are added to water, they form lipid bilayer structures (liposomes) that contain an aqueous core surrounded by a hydrophobic membrane. This novel structure can deliver water insoluble drugs that are "dissolved" in its hydrophobic membrane or, alternatively, water soluble drugs can be encapsulated within its aqueous core. This strategy has been employed in a number of fields. For example, liposomes have been used as drug carriers since they are rapidly taken up by the cells and, moreover, by the addition of specific molecules to the liposomal surface they can be targeted to certain cell types or organs, an approach that is typically used for drugs that are encapsulated in the aqueous core. For cosmetic applications, phospholipids and lipid substances are dissolved in organic solvent and, with solvent removal, the resulting solid may be partially hydrated with water and oil to form a cosmetic cream or drug-containing ointment. Finally, liposomes have been found to stabilize certain food ingredients, such as omega-3 fatty acid-containing fish oils to reduce oxidation and rancidity (Haynes et al, U.S. Pat. No. 5,139,803).

In an early description of liposome formulation (Bangham et al., 1965 J. Mol. Biol. 13, 238-252), multilammelar vesicles were prepared by the addition of water and mechanical energy to the waxy film that was formed by removing the organic solvent that was used to dissolve the phospholipids. In later work, it was found that the combination of sterols (cholesterol, phytosterols) and phospholipids allowed the formulation of liposomes with more desirable properties, such as enhanced stabilization and encapsulation efficiency. The patent and scientific literature describe many methodological improvements to this general strategy. However, none presently known achieves the efficient delivery rates of the present invention.

Even though liposomes provide an elegant method for drug delivery, their use has been limited by cumbersome preparation methods and the inherent instability of aqueous preparations. A number of patents describe the large scale preparation of pre-liposomal components that can be hydrated later to form the desired aqueous-based delivery vehicle. Evans et al. (U.S. Pat. No. 4,311,712) teach that all the components (phospholipids, cholesterol and biological agent) can be mixed in an organic solvent with a melting point near that of room temperature. After solvent removal by lyophilization, addition of water produced liposomes with the biologically active material "dissolved" in the membrane. Similarly, U.S. Pat. No. 5,202,126 (Perrier et al.) teaches the addition of all the components in the organic phase, but with solvent removal accomplished by atomization following the method described by Redziniak et al. (U.S. Pat. Nos. 4,508,703 and 4,621,023). The pulverulent solid so produced can then by hydrated, homogenized and converted into a cream for the typical delivery of the biologically active material, in this case pregnenolone of pregnenolone ester. Orthoefer describes the preparation of liquid crystal phospholipids (U.S. Pat. No. 6,312,703) as a novel carrier for biologically active compounds. In this method, the various solid components are pre-mixed and then subjected to high pressure to form a lecithin bar that can be used in cosmetic applications as soap or the pressurized components can be extruded as a rope and cut into pharmaceutical-containing tablets. Unlike previous work, this method does not teach premixing in organic solvent or homogenization in water.

The utility of a dried preparation to enhance the stability and shelf life of the liposome components has long been recognized, and numerous methods have been devised to maintain the stability of liposomal preparations under drying conditions. Schneider (U.S. Pat. No. 4,229,360) describes the preparation of encapsulated insulin in liposomes by adding the aqueous peptide solution to a film of phospholipids. Lyophilization of this liposomal mixture in the presence of gum Arabic or dextran produced a solid that could be reconstituted with water to form liposomes. However, following a similar procedure to encapsulate cyclosporine, Rahman et al. (U.S. Pat. No. 4,963,362) teach that the lyophilization step can be performed without the addition of other additives, such that the re-hydrated liposomes maintain their ability to encapsulate the bioactive substance. Vanlerberghe et al. (U.S. Pat. No. 4,247,411) teach a similar process, but include sterols with the phospholipids to provide a more stable liposome. In an effort to enhance the stability and dispersibility of liposomes in a solid matrix, Payne et al. (U.S. Pat. Nos. 4,744,989 and 4,830,858) describe methods for coating a water soluble carrier, such as dextrose, with a thin film of liposome components. When added to water, the carrier dissolves and the liposome components hydrate to form liposomes.

The goal of all these methods is to produce a solid that can be re-hydrated at a later time to form liposomes that can deliver a biologically active substance to a target tissue or organ. Surprisingly, there have been only two reports that use the dried liposome preparations themselves, with no intermediate hydration, as the delivery system. Ostlund, U.S. Pat. No. 5,932,562 teaches the preparation of solid mixes of plant sterols for the reduction of cholesterol absorption. Plant sterols or plant stanols are premixed with lecithin or other amphiphiles in organic solvent, the solvent removed and the solid added back to water and homogenized. The emulsified solution is dried and dispersed in foods or compressed into tablets or capsules. In this case, the active substance is one of the structural components of the liposome itself (plant sterol) and no additional biologically active substance was added. Manzo et al. (U.S. Pat. No. 6,083,529) teach the preparation of a stable dry powder by spray drying an emulsified mixture of lecithin, starch and an anti-inflammatory agent. When applied to the skin, the biologically active moiety is released from the powder only in the presence of moisture. Neither Ostlund nor Manzo suggest or teach the use of sterol, and lecithin and a drug active, all combined with a non-polar solvent and then processed to provide a dried drug carrying liposome of enhanced delivery rates.

Substances other than lecithin have been used as dispersing agents. Following the same steps (dissolution in organic solvent, solvent removal, homogenization in water and spray drying) as those described in U.S. Pat. No. 5,932,562, Ostlund teaches that the surfactant sodium steroyl lactylate can be used in place of lecithin (U.S. Pat. No. 6,063,776) Burruano et al. (U.S. Pat. Nos. 6,054,144 and 6,110,502) describe a method of dispersing soy sterols and stanols or their organic acid esters in the presence of a mono-functional surfactant and a poly-functional surfactant without homogenization. The particle size of the solid plant-derived compounds is first reduced by milling and then mixed with the surfactants in water. This mixture is then spray dried to produce a solid that can be readily dispersed in water. Similarly, Bruce et al. (U.S. Pat. No. 6,242,001) describe the preparation of melts that contain plant sterols/stanols and a suitable hydrocarbon.

On cooling these solids can be milled and added to water to produce dispersible sterols. Importantly, none of these methods anticipate the type of delivery method described here as a means to delivery hydrophobic, biologically active compounds.

All of the above described art, either deals with lowering of cholesterol or with a variety of techniques used in an attempt to solubilize some hydrophobic drugs using specific lipids. None teach or suggest a generalized approach to enhance solubilization in a water environment and to enhance the rate of diffusion of hydrophobic drugs through lipid membranes of cell walls so that the drug has increased bio availability at any given dose.

The above described art describing solubilizing hydrophobic drugs is focused on creating an artificial membrane whose composition does not correspond to that found in natural, cellular structures. For example, previous preparations describe a mixture in which a sterol is incorporated in the phospholipid (amphiphile) phase at a weight ratio of between 1% and 20%, and preferably of 10% [Perrier et al., U.S. Pat. No. 5,202,126 (c2, line 33)], a prejudice that is re-affirmed in later work [Meybeck & Dumas, U.S. Pat. No. 5,290,562 (c3, line 29)]. While these ratios provide useful properties for the intended low drug loading use of this delivery system, they do not provide sufficient capacity for higher drug loading. In erythrocyte plasma membrane, liver plasma membrane or myelin, the ratio of cholesterol to phosphatidyl choline is close to one and the ratio of cholesterol to all membrane phospholipids is usually less than three. While the reason for these ratios is not known it is speculated that this combination stabilizes the membrane and allows highly hydrophobic proteins to span the lipid portion of the membrane. Based on these considerations from native cellular membranes, the present applicant explored the ratios set forth herein.

Further, in contrast to the above described art, this invention reveals that the ratio of the amphiphile to the drug and plant sterol combination also plays an unexpected role for the delivery of this class of drug substance. In order to form creams and parenteral liposomal preparations, previous work focused on the preparation of dispersions containing small liposomal particles (less than 1 µm) by maintaining a high ratio of lecithin to the other components. This prejudice is shown by the requirement that the sum of the drug and the sterol present should not exceed about 25% and preferably about 20% of the total lipid phase present. Hence, the previous art teaches a ratio of lecithin to the sum of the sterol and drug components of at least 3.0, and preferably 4.0 [Perrier et al., U.S. Pat. No. 5,202,126 (c2, line 45), Meybeck & Dumas, U.S. Pat. No. 5,290,562 (c3, line 29)]. While this preferred ratio of lecithin to the other components may be appropriate for certain delivery systems, such as creams, ointments and parenteral liposomal preparations, a simple calculation demonstrates its potential impracticality when applied to a conventional solid delivery system, such as certain food products, tablets and capsules. For example, if 100 mg of drug is required for an efficacious dose and if 100 mg of sterol is included, then according to the specifications, at least 800 mg of lecithin is needed to give a total mass of 1.0 gm. Excipients must then be added to provide a compressible and flowable powder matrix for compression or encapsulation. The resulting delivery system requires many tablets or capsules in order to deliver the active drug substance, leading to high costs and poor subject compliance. Thus, in practical terms, the previous method is severely limited and useful only for creams, ointments and parenteral liposome aqueous preparations or to solid formulations (tablets and capsules) of poorly soluble drugs that have very high potency and that can be delivered in very small doses.

In previous art, the selection of an acceptable ratio of ingredients was determined by the particle size of the dispersion after homogenization and the subsequent stability of that dispersion with time and temperature. As measured by the mean size and polydispersity, there is prejudice against those dispersions that change over time and that undergo sedimentation. Importantly, to maintain liposomal "quality," the dispersion must be characterized by a small particle size to enhance the stability of the dispersion for intended uses [Perrier et al., U.S. Pat. No. 5,202,126 (c4, line 61)]. Departure from this preferred ratio produces sediment which "detracts from the stability of the liposomes"[Perrier et al., U.S. Pat. No. 5,202,126, (c5, line 10)]. Sediments, so formed, are considered sub-optimal and are discarded as inappropriate for further use.

An object of this invention is to enhance the usefulness of a hydrophobic drug substance by its combination with sterols such that the ratio of these two components to an amphiphile is chosen to produce liposomal particles greater than 1 µm. This combination, which produces a particle dispersion that would be characterized by previous criteria as low quality and of little usefulness, has surprising and unexpected utility. Thus, this combination produces a delivery system with the following useful, novel and unexpected advantages: (1) a dispersed solution that can be dried and re-hydrated to produce a dispersion of particles that is similar to the dispersion from which it was derived, without re-addition of energy; (2) high drug loading capacity by minimizing the amount of amphiphile in the mix; (3) a dispersed solution that is stable to conventional drying methods without the addition of large amounts of stabilizers. In addition, the dried solid so manufactured can be easily added to a food product or compacted in a tablet or capsule to render the hydrophobic drug bioavailable on ingestion and easily deliverable in a pharmaceutical format.

A dispersion consisting of large particles is consistent with currently held theories on the physical chemical and biochemical events that occur in fat digestion and provide a framework for understanding the basis for enhanced lipid drug absorption described here. Large emulsion particles containing a variety of fats, fat soluble vitamins and lipid nutrients enter the small intestine from the stomach. For example, the fat globules in bovine and human milk have diameters of 1-10 µm and 1.5-4 µm, respectively, similar in size to the phospholipid sterol drug dispersions described here, but larger than those described in previous patent applications (Patton & Keenan, Biochim Biophys Acta, 1975, 415: 273-309; Hamosh et al., Pediatrics, 1984, 75(suppl): 146-150). In the small intestinal lumen, the globule dispersions are exposed to bile salt, additional phospholipid and a variety of enzymes and proteins that serve to reduce the particle size in a controlled series of hydrolytic and physical chemical steps. In the presence of excess bile salt, small vesicles and/or liquid crystals are formed that become saturated with lipolytic products and fat soluble nutrients, which provides a thermodynamically favorable environment for maximum rates of lipid uptake (Thomson et al., Can J Physiol Pharmacol, 1989, 67: 179-191). Packaging a water insoluble drug in a sterol amphiphile matrix characterized as a dispersion of large particles may allow the same absorptive steps to occur that are used by naturally occurring lipids and nutrients found in the diet. Importantly, addition of small particles may not be compatible with one or more steps of this absorption process and may lead to less efficient uptake.

SUMMARY OF THE INVENTION

A general method and delivery composition is provided for enhancing the bioavailability of hydrophobic, poorly water soluble compound and drugs, using the following steps and materials:

(a) An amphiphile, such as lecithin or one of its derivatives, a sterol (preferably a plant-derived sterol and most preferably a reduced plant-derived sterol) and a selected drug are mixed in a non-polar solvent (preferably ethyl acetate or heptane) at its boiling point;

(b) a solid residue is collected after the solvent is driven off at elevated temperature to maintain the solubility of all the components;

(c) the solid residue is broken into small pieces and dispersed with vigorous stirring in water to form a milky solution at a temperature that is less than the decomposition temperature of any one of the components or the boiling point of water, whichever is lower;

(d) the milky solution is passed through a homogenizer, such as a Gaulin Dairy Homogenizer (or suitable equivalent) operating at maximum pressure; and thereafter (e) a suitable drying aid is added (e.g. Maltrin, Capsule M or suitable equivalent) and then the milky solution is spray dried or lyophilized to produce a solid that can be incorporated into food products or into tablets or capsules, providing the appropriate excipients are added.

In another alternative method, the amphiphile, plant sterols and active drug are mixed in the presence of an organic solvent such as hexane or ethyl acetate, the solvent removed and the solid compressed and extruded for the formulation of tablets and capsules.

The formulation method described contains a minimum of three components, an emulsifier(s), a sterol and a hydrophobic active or drug compound.

DETAILED DESCRIPTION OF A PREFERRED EMBODIMENT

Numerous amphiphilic emulsifiers have been described, but since this invention contemplates pharmaceutical and food applications only those compounds that have been approved for human use are acceptable. A preferred emulsifier is lecithin derived from egg yolk, soy beans or any of its chemically modified derivatives, such as lysolecithin. Lecithin and its modified derivatives are not only excellent emulsifiers and surfactants, they also have many health benefits that are beneficial when used as the contemplated pharmaceutical formulation agent described here [Cevc, G. and Paltauf, F., eds., "Phospholipids: Characterization, Metabolism, and Novel Biological Applications", pp. 208-227 AOCS Pres, Champaign, Ill., 1995]. While many grades and forms are available, de-oiled lecithin produces the most consistent results Typical commercially available examples are Ultralec P, Ultralec F and Ultralec G (Archer Daniels Midland, Decatur, Ill.) or Precept 8160, a powdered, enzyme-modified lecithin (Central Soya, Fort Wayne, Ind.).

Other emulsifiers can be successfully used including, but not limited to mono and diglycerides, diacetyltartaric acid esters of mono and diglycerides, monoglyceride phosphate, acetylated monoglycerides, ethoxylated mono and diglycerides, lactylated monoglycerides, propylene glycol esters, polyglycerol esters, polysorbates, sorbitan esters, sodium and calcium stearoyl lactylate, succinylated monoglycerides, sucrose esters of fatty acids, fatty alcohols, sodium salts of fatty acids. In certain instances combinations of these emulsifiers may also be used.

A variety of sterols and their ester derivatives can be added to the emulsifier(s) to enhance the aqueous dispersibility in the gut in the presence of bile salts and bile phospholipid. While cholesterol has frequently been used for this purpose, its absorption can lead to elevated LDL-cholesterol levels, making it a poor choice for the pharmaceutical applications contemplated here. Plant-derived sterols, especially those derived from soy and tall oil, are the preferred choice since they have been shown to lower LDL-cholesterol and they are considered to be safe [Jones P. J. H., McDougall, D. E., Ntanios, F., & Vanstone, C. A. (1996) Dietary phytosterols as cholesterol-lowering agents in humans. Can. J. Physiol. Pharmacol. 75, 227]. Specifically, this invention contemplates the use of mixtures including, but not limited to sitosterol, campesterol, stigmasterol and brassicasterol and their corresponding fatty acid esters prepared as described elsewhere (Wester I., et al., "Stanol Composition and the use thereof", WO 98/06405). The reduced forms of the above-mentioned sterols and their corresponding esters are the most preferred, since they also lower human LDL-cholesterol and their absorption is from five- to ten-fold less than that of their non-reduced counterparts [Ostlund R E., et al., (2002), Am. J. of Physiol., 282, E 911; Spilburg et al., 4$^{th}$ International Symposium of the Role of Soy in Preventing and Treating Chronic Disease, Nov. 4-7, 2002, in Diego Calif. Abstract D4].

Hydrophobic drug or potential drugs may be selected from any therapeutic class including but not limited to anesthetics, anti-asthma agents, antibiotics, antidepressants, anti-diabetics, anti-epileptics, anti-fungals, anti-gout, anti-neoplastics, anti-obesity agents, anti-protozoals, anti-phyretics, anti-virals, anti-psychotics, calcium regulating agents, cardiovascular agents, corticosteroids, diuretics, dopaminergic agents, gastrointestinal agents, hormones (peptide and non-peptide), immunosuppressants, lipid regulating agents, phytoestrogens, prostaglandins, relaxants and stimulants, vitamins/nutritionals and xanthines. A number of criteria can be used to determine appropriate candidates for this formulation system, including but not limited t the following: drugs or organic compounds that are known to be poorly dispersible in water, leading to long dissolution times; drugs or organic compounds that are known to produce a variable biological response from dose to dose; drugs or organic compounds that have been shown to be preferentially soluble in hydrophobic solvent as evidenced by their partition coefficient in the octanol water system or; drugs that are preferentially absorbed when consumed with a fatty meal.

In addition to these components, other ingredients may be added that provide beneficial properties to the final product, such as vitamin E to maintain stability of the active species.

All the components are dissolved in a suitable non-polar organic solvent, such as chloroform, dichloromethane, ethyl acetate, pentane, hexane, heptane or supercritical carbon dioxide. The choice of solvent is dictated by the solubility of the components and the stability of the drug at the temperature of the solvent. The preferred solvents are non-chlorinated and for heat stable compounds, heptane is the most preferred solvent because of its high boiling point, which increases the overall solubility of all the components.

The weight ratio of the components in the final mixture depends on the nature of the hydrophobic compound, but regardless of its structure or other properties the goal is to produce an emulsified mixture of drug, sterols and amphiphile that has a mean particle size of at least 1.0 μm. To achieve this end, the amount of amphiphile in the system is minimized relative to the other two components so that the ratio of amphiphile to the drug sterol combination is 3.0 or less. On the other hand, sufficient amphiphile must be present to allow emulsification such that the ratio of amphiphile to the sterol drug combination is 0.05 or greater.

After all the components are dissolved at the desired ratio in the appropriate solvent, the liquid is removed at elevated temperature to maintain the solubility of all the components. Residual solvent can be removed by pumping under vacuum. Alternatively, the solvent can be removed by atomization as describe in U.S. Pat. Nos. 4,508,703 and 4,621,023. The solid is then added to water at a temperature that is less than the decomposition temperature of one of the components or the boiling point of water, whichever is lower. The mixture is vigorously mixed in a suitable mixer to form a milky solution, which is then homogenized, preferably with a sonicator, Gaulin dairy homogenizer or a microfluidizer. The water is then removed by spray drying, lyophilization or some other suitable drying method. Before drying, it is helpful but not necessary, to add maltrin, starch, silicon dioxide or calcium silicate to produce a flowable powder that has more desirable properties for filling capsules, compression into tablets or addition to food products.

There are other known methods that can be used to prepare tablets. After the components have been mixed at the appropriate ratio in organic solvent, the solvent can be removed as described above. The solid material so prepared can then be compressed at elevated pressure and extruded into a rope. The rope can be cut in segments to form tablets. This method is similar to that described in U.S. Pat. No. 6,312,703, but the inventor did not recognize the importance of pre-mixing the components in organic solvent. While this previous method produces a tablet, the components may not be as freely dispersible in bile salt and phospholipid when they are not pre-mixed in organic solvent. Alternatively, the solid material that results from homogenization and spray drying can be compressed at high pressure and extruded to form a rope that can be cut into tablets.

The precise details of tableting technique are not a part of this invention, and since they are well-known they need not be described herein in detail. Generally pharmaceutical carriers which are liquid or solid may be used. The preferred liquid carrier is water. Flavoring material may be included in the solutions as desired.

Solid pharmaceutical carriers such as starch, sugar, talc, mannitol and the like may be used to form powders. Mannitol is the preferred solid carrier. The powders may be used as such for direct administration to a patient, or instead, the powders may be added to suitable foods and liquids, including water, to facilitate administration.

The powders also may be used to make tablets, or to fill gelatin capsules. Suitable lubricants like magnesium stearate, binders such as gelatin, and disintegrating agents like sodium carbonate in combination with citric acid may be used to form the tablets.

While not precisely knowing why, and not wishing to be bound by any theory of operability, the fact is that for difficulty soluble drugs this composition and combination of steps achieved higher absorption rates.

EXAMPLE

Preparation of Formulated Cyclosporin

Cyclosporin A (0.50 gm) phospholipid (Ultralec, 1.00 gm) and soy stanols (0.50 gm) were mixed in a 30 mL Corex glass tube to give a weight ratio of emulsifier to drug stanol combination of 1.0. Ethyl acetate (5.0 mL) was added to the tube and the mixture was warmed on a water bath of 60° C. until all the solids dissolved. The clear solution was mixed thoroughly with a vortexer and the solvent was removed under a stream of nitrogen, with occasional warming to 60° C. to enhance the removal of ethyl acetate solvent. Residual solvent was removed from the solid under vacuum. After the sample was thoroughly dried, water (10 mL) was added and the mixture was sonicated for four minutes to produce a creamy solution. Maltrin (500 mg) was dissolved in 3 mL of water and added to the creamy solution with mixing. After removing an aliquot for particle size analysis, the remaining solution was frozen in a dry ice acetone bath and lyophilized. An aliquot of the lyophilized material was re-dissolved in water and the particle size distribution of this re-hydrated material was determined and compared to that of the sonicated mixture from which it was derived. As shown in the Table below, the particle size distribution of the re-hydrated sample indicates that drying and rehydration do not alter significantly the particle size distribution when compared to that of the starting material.

| Preparation | D[v, 0.1]* | D[v, 0.5] | D[v, 0.9] |
|---|---|---|---|
| Hydrated Formulated Cyclosporin | 4.13 | 14.20 | 45.04 |
| Emulsion, Dried and Re-hydrated | 4.05 | 9.90 | 26.58 |

*10% of the particles have a particle size less than this value in μm. The other parameters refer to the particle size for 50% and 90% of the particles, respectively.

Preparation of Capsules Containing Formulated Solid Cyclosporin.

Formulated Cyclosporin A (125 mg), starch (75 mg), $CaCO_3$ (50 mg) and $SiO_2$ (3 mg) were mixed together and packed into a #1 gelatin capsule. When the gelatin capsule was added with stirring to 37° C. water, the powder dispersed within 10 minutes after the capsule dissolved.

Assessment of Bioavailability in Dogs.

Two dogs were dosed with 25 mg of Neoral capsules (Sandimmune) and two dogs were given 25 mg of encapsulated formulated Cyclosporin A (1.25 mg/kg/day). At 0, 1, 2, 4, 8, 12 and 24 hours post administration, blood was drawn into tubes containing EDTA. After a washout period of at least 72 hours, the animals were given the alternate dose and the blood draws were repeated at the same time intervals. When all the samples were collected, they were assayed for Cyclosporin, using the Cyclo-Trac SP assay (Diasorin, Stillwater, Minn.). When cyclosporine A was formulated in this way, the area under the blood concentration-time curve was about 67% of that found for Neoral administration. The peak concentration of the blood concentration-time curve occurred at 4 hours for the formulated cyclosporin versus 2 hours for Neoral, reflecting a longer dissolution time of the solid.

It should be understood that certain modifications should be and will be apparent to those of ordinary skill in the art of pharmacology, and that such modifications to the precise procedures and compositions set forth herein are invention, either literally or by the Doctrine of Equivalents. In this light, the following claims are made.

What is claimed is:

1. A solid, anhydrous drug delivery composition for normally difficulty soluble hydrophobic drug actives, which when added to water create suspended drug active containing liposomes having a mean particle size of at least 1.0 micron, comprising:
   lecithin;
   a sterol, a stanol, a sterol ester, or a stanol ester;
   a drug active effective amount of a hydrophobic drug active with the weight ratio of lecithin to the sterol, stanol, sterol ester, stanol ester and hydrophobic drug active combination being 1.0;
   said delivery composition enhancing the uptake of the hydrophobic drug active through small intestinal membranes.

2. The composition of claim 1 wherein the sterol, stanol, sterol ester, or stanol ester is selected from the group consisting of cholesterol, derivatives of cholesterol, a plant sterol, a plant stanol, a plant sterol ester, a plant stanol ester, and combinations thereof.

3. The composition of claim 1 wherein the hydrophobic drug is selected from the group consisting of: anesthetics, anti-asthma agents, antibiotics, antidepressants, anti-diabetics, anti-epileptics, anti-fungals, anti-gout agents, anti-neoplastics, anti-obesity agents, anti-protozoals, anti-pyretics, anti-virals, anti-psychotics, calcium regulating agents, cardiovascular agents, corticosteroids, diuretics, dopaminergic agents, gastrointestinal agents, hormones, immunosuppressants, lipid regulating agents, phytoestrogens, prostaglandins, relaxants, stimulants, vitamins, nutritional agents, and xanthines.

4. The drug delivery composition of claim 2, wherein the plant sterol, sterol ester, stanol, or stanol ester is derived from a vegetable oil source.

5. The composition of claim 1 wherein the drug delivery composition further comprises Vitamin E as an additional hydrophobic compound.

6. The composition of claim 1, wherein the lecithin is soy lecithin or egg lecithin.

7. A solid, anhydrous drug delivery composition for cyclosporin, which when added to water creates suspended cyclosporin containing liposomes having a mean particle size of at least 1.0 micron, comprising:
   lecithin;
   a sterol, a stanol, a sterol ester, or a stanol ester;
   a drug active effective amount of cyclosporin with the weight ratio of lecithin to the sterol, sterol ester, stenol, or stenol ester, in combination with cyclosporin combination being 1.0.

8. The composition of claim 7 wherein the sterol, stanol, sterol ester, or stanol ester is selected from the group consisting of cholesterol, derivatives of cholesterol, a plant sterol, a plant stanol, a plant sterol ester, a plant stanol ester, and combinations thereof.

9. The composition of claim 8, wherein the plant sterol, stanol, sterol ester, or stanol ester is derived from a vegetable oil source.

10. The composition of claim 7, wherein the lecithin is soy lecithin or egg lecithin.

11. A method of preparing the solid, anhydrous drug delivery composition of claim 1 for normally difficulty soluble hydrophobic drug actives, comprising:
   mixing said lecithin, said sterol, stanol, sterol ester, or stanol ester, and said hydrophobic drug active, with a non-polar organic solvent, with the weight ratio of said lecithin to the sterol, stanol, sterol ester, or stanol ester, and hydrophobic drug active combination being 1.0;
   removing the solvent to leave a solid residue of the mixed components;
   adding water to the solid residue of the mixed components at a temperature less than the decomposition temperature of any one of the mixed components;
   homogenizing the aqueous mixture to create liposomes having a mean particle size of at least 1.0 micron;
   drying the homogenized mixture; and
   providing the dried solid residue of the mixed components in a solid pharmaceutical carrier format.

12. The method of claim 11 wherein the non-polar organic solvent is selected from the group consisting of ethyl acetate and heptane.

13. The method of claim 11 wherein the non-polar organic solvent is selected from the group consisting of heptane, chloroform, dichloromethane, isopropanol and supercritical carbon dioxide.

14. The method of claim 11 wherein the non-polar organic solvent is removed from the mix by elevating the temperature at or above the solvent's boiling point.

15. The method of claim 11 wherein the solvent removal continues until a solid residue that contains less than 0.5% solvent is provided.

16. The method of claim 15 wherein the solid formed after solvent removal is pulverized to produce a dispersible powder.

17. The method of claim 15 wherein the dried solid residue of the mixed components is dispersed in liquid water with vigorous stirring at a temperature less than the decomposition temperature of any of the mixed components.

18. The method of claim 11 wherein the aqueous mixture is homogenized in a homogenizer selected from the group consisting of a Gaulin homogenizer, a French press, a sonicator, and a microfluidizer.

19. The method of claim 11 wherein the homogenized aqueous mixture is dried in a drier selected from the group consisting of spray driers and lyophilizers.

20. A method of preparing the solid, anhydrous drug delivery composition of claim 7 for cyclosporin, comprising:
   mixing said lecithin, said sterol, stanol, sterol ester, or stanol ester, and said cyclosporine with a non-polar organic solvent, with the weight ratio of lecithin to the sterol, stanol, sterol ester, or stanol ester and cyclosporin combination being 1.0;
   removing the solvent to leave a solid residue of the mixed components;
   adding water to the solid residue of the mixed components at a temperature less than the decomposition temperature of any one of the mixed components;
   homogenizing the aqueous mixture to create liposomes having a mean particle size of at least 1.0 micron;
   drying the homogenized mixture; and
   providing the dried solid residue of the mixed components in a solid pharmaceutical carrier format.

* * * * *